US011648075B2

(12) United States Patent
Peine

(10) Patent No.: US 11,648,075 B2
(45) Date of Patent: May 16, 2023

(54) ROBOTIC SURGICAL SYSTEM CONTROL ARM INCLUDING DUAL ENCODERS

(71) Applicant: Covidien LP, Mansfield, MA (US)

(72) Inventor: William Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 387 days.

(21) Appl. No.: 16/643,189

(22) PCT Filed: Sep. 4, 2018

(86) PCT No.: PCT/US2018/049319
§ 371 (c)(1),
(2) Date: Feb. 28, 2020

(87) PCT Pub. No.: WO2019/050822
PCT Pub. Date: Mar. 14, 2019

(65) Prior Publication Data
US 2020/0179070 A1    Jun. 11, 2020

Related U.S. Application Data

(60) Provisional application No. 62/554,208, filed on Sep. 5, 2017.

(51) Int. Cl.
A61B 34/00    (2016.01)
A61B 34/37    (2016.01)
(Continued)

(52) U.S. Cl.
CPC .............. A61B 34/74 (2016.02); A61B 34/37 (2016.02); A61B 34/76 (2016.02);
(Continued)

(58) Field of Classification Search
None
See application file for complete search history.

(56) References Cited

U.S. PATENT DOCUMENTS 5,954,692 A    9/1999  Smith et al.
6,252,368 B1   6/2001  Sugie
(Continued)

FOREIGN PATENT DOCUMENTS

EP    2911832 A1     9/2015
KR    101369286 B1   3/2014
(Continued)

OTHER PUBLICATIONS

International Search Report dated Jan. 2, 2019 and Written Opinion completed Jan. 2, 2019 corresponding to counterpart Int'l Patent Application PCT/US2018/049319.
(Continued)

Primary Examiner — Tamara L Weber
(74) Attorney, Agent, or Firm — Carter, DeLuca & Farrell LLP

(57) ABSTRACT

A control arm of a robotic surgical system includes a member, a drive motor, a first joint encoder, and a controller. The member is supported about a first joint. The drive motor is operably coupled to the member and configured to rotate the member about the first joint. The first joint encoder is disposed about the first joint and configured to transmit position signals indicative of the position of the member about the first joint. The controller is configured to transmit control signals in response to receiving position signals from the first joint encoder, the control signals causing the drive motor to overcome friction associated with the motion of the member about the first joint.

15 Claims, 8 Drawing Sheets

(51) Int. Cl.
    *A61B 34/10*    (2016.01)
    *A61B 34/20*    (2016.01)
    *A61B 34/30*    (2016.01)

(52) U.S. Cl.
    CPC . *A61B 2034/101* (2016.02); *A61B 2034/2059* (2016.02); *A61B 2034/305* (2016.02); *A61B 2034/742* (2016.02)

(56) References Cited

U.S. PATENT DOCUMENTS

| | | | |
|---|---|---|---|
| 6,437,771 | B1 | 8/2002 | Rosenberg et al. |
| 7,846,103 | B2 | 12/2010 | Cannon, Jr. et al. |
| 7,963,433 | B2 | 6/2011 | Whitman et al. |
| 8,828,023 | B2 | 9/2014 | Neff et al. |
| 8,992,565 | B2 | 3/2015 | Brisson et al. |
| 2004/0183777 | A1 | 9/2004 | Bevirt et al. |
| 2007/0046677 | A1 | 3/2007 | Hong et al. |
| 2007/0287992 | A1* | 12/2007 | Diolaiti .................. A61B 34/71 606/1 |
| 2009/0248042 | A1 | 10/2009 | Kirschenman |
| 2011/0240714 | A1 | 10/2011 | Whitman et al. |
| 2012/0245595 | A1 | 9/2012 | Kesavadas et al. |
| 2013/0069581 | A1 | 3/2013 | Lim et al. |
| 2014/0156074 | A1* | 6/2014 | Seo ........................... B25J 3/04 700/257 |
| 2015/0018622 | A1 | 1/2015 | Tesar et al. |
| 2015/0051130 | A1 | 2/2015 | Blizzard |
| 2015/0248121 | A1 | 9/2015 | Nilsson |
| 2016/0375577 | A1 | 12/2016 | Louveau |
| 2017/0027655 | A1 | 2/2017 | Niemeyer |
| 2017/0224428 | A1 | 8/2017 | Kopp |
| 2018/0014897 | A1 | 1/2018 | Peine |
| 2019/0125462 | A1 | 5/2019 | Peine et al. |
| 2019/0192239 | A1* | 6/2019 | Xu .................. A61B 17/00234 |
| 2019/0321112 | A1 | 10/2019 | Cecil |

FOREIGN PATENT DOCUMENTS

| | | |
|---|---|---|
| WO | 2016053657 A1 | 4/2016 |
| WO | 2016133633 A1 | 8/2016 |

OTHER PUBLICATIONS

Extended European Search Report dated Apr. 13, 2021 corresponding to counterpart Patent Application EP 18854678.2.
Indian Office Action dated Feb. 24, 2022 corresponding to counterpart Patent Application IN 202017008957.
Japanese Office Action dated Aug. 12, 2022 issued in corresponding JP Application No. 2020-534808.
Chinese Office Action dated Jan. 29, 2023, issued in corresponding Chinese Appln. No. 201880060635, 12 pages.

* cited by examiner

ROBOTIC SURGICAL SYSTEM CONTROL ARM INCLUDING DUAL ENCODERS

CROSS-REFERENCE TO RELATED APPLICATIONS

This application is a U.S. National Stage Application filed under 35 U.S.C. § 371(a) of International Patent Application Ser. No. PCT/US2018/049319, filed Sep. 4, 2018, which claims the benefit of and priority to U.S. Provisional Patent Application Ser. No. 62/554,208, filed Sep. 5, 2017, the entire disclosure of which is incorporated by reference herein.

BACKGROUND

Robotic surgical systems have been used in minimally invasive medical procedures. During such medical procedures, the robotic surgical system is controlled by a surgeon or clinician interfacing with a user interface of the robotic surgical system. The user interface or console allows the clinician to manipulate and end effector associated with the surgical system acting on the patient.

The user console includes one or more control arms which support an input handle or gimbal that is movable by the clinician to control the robotic surgical system. The control arms transmit signals to a controller which correspond to the position or pose of the control arms in a workspace during the medical procedure. The controller may transmit force feedback to the input handles via one or more motors that are operably coupled to the input handles by a transmission. The transmission can required additional forces be applied by a clinician to overcome frictional forces within the transmission. Where additional forces are required, the input handle may be perceived as "heavy" by the clinician during a surgical procedure.

SUMMARY

This disclosure relates generally to systems and methods that compensate for frictional forces within the transmission associated with the control arm of a robotic surgical system.

In accordance with an aspect of the present disclosure, a control arm of a robotic surgical system includes a member, a drive motor, a first joint encoder, and a controller. The member is supported about a first joint. The drive motor is operably coupled to the member and is configured to rotate the member about the first joint. The first joint encoder is disposed about the first joint and is configured to transmit position signals indicative of a pose of the member about the first joint. The controller is configured to transmit control signals in response to receiving position signals from the first joint encoder.

In aspects, the control arm further includes a transmission component. The transmission component may be disposed between the drive motor and the first joint to couple the member to the drive motor. The controller may be configured to transmit control signals to overcome a friction associated with the transmission component for moving the member about the first joint.

According to aspects, the control arm includes a motor encoder configured to transmit motor position signals to the controller. The drive motor may be coupled to the transmission component at a second joint. The motor encoder may be coupled to the drive motor at the second joint.

According to aspects, the controller is configured to calculate a direction of the member moving about the first joint. The controller may be configured to generate control signals to overcome transmission friction in response to calculating the direction of the member moving about the first joint. The controller may also be configured to calculate a velocity of the member moving about the first joint. The controller may be configured to generate control signals to overcome transmission friction in response to calculating the direction and the velocity of the member about the first joint.

According to aspects of the present disclosure, a method of compensating for friction in a transmission component includes receiving first position information of a member moving about a first joint from a joint encoder disposed about the first joint, calculating a first direction and a first velocity of the member in response to receiving the first position information, and transmitting control signals to a drive motor to overcome transmission friction associated with the transmission component cooperating with movement of the member. The member is coupled to the drive motor at the first joint by a transmission component.

In aspects, the method includes receiving second position information from the joint encoder in response to the member moving about the first joint, calculating a second direction and a second velocity of the member moving about the first joint, and comparing the first direction to the second direction.

In certain aspects, the method includes transmitting control signals to move the drive motor a predetermined distance in the second direction when the first direction is different from the second direction.

According to aspects of the present disclosure, a method of compensating for positional offsets between a member and a drive motor includes receiving first position information from a first joint encoder disposed about a first joint, calculating a first direction of movement of the member about the first joint, receiving second position information from the first joint encoder, calculating a second direction of movement of the member about the first joint, comparing the first direction of movement to the second direction of movement, and transmitting control signals to move the drive motor a predetermined distance in the first direction of movement when the first direction of movement is different from the second direction of movement. The first joint operably couples the member to the drive motor at the first joint. In aspects, the drive motor is coupled to a transmission component at a second joint. The predetermined distance may be equal to an offset distance.

DETAILED DESCRIPTION

Figure 1:
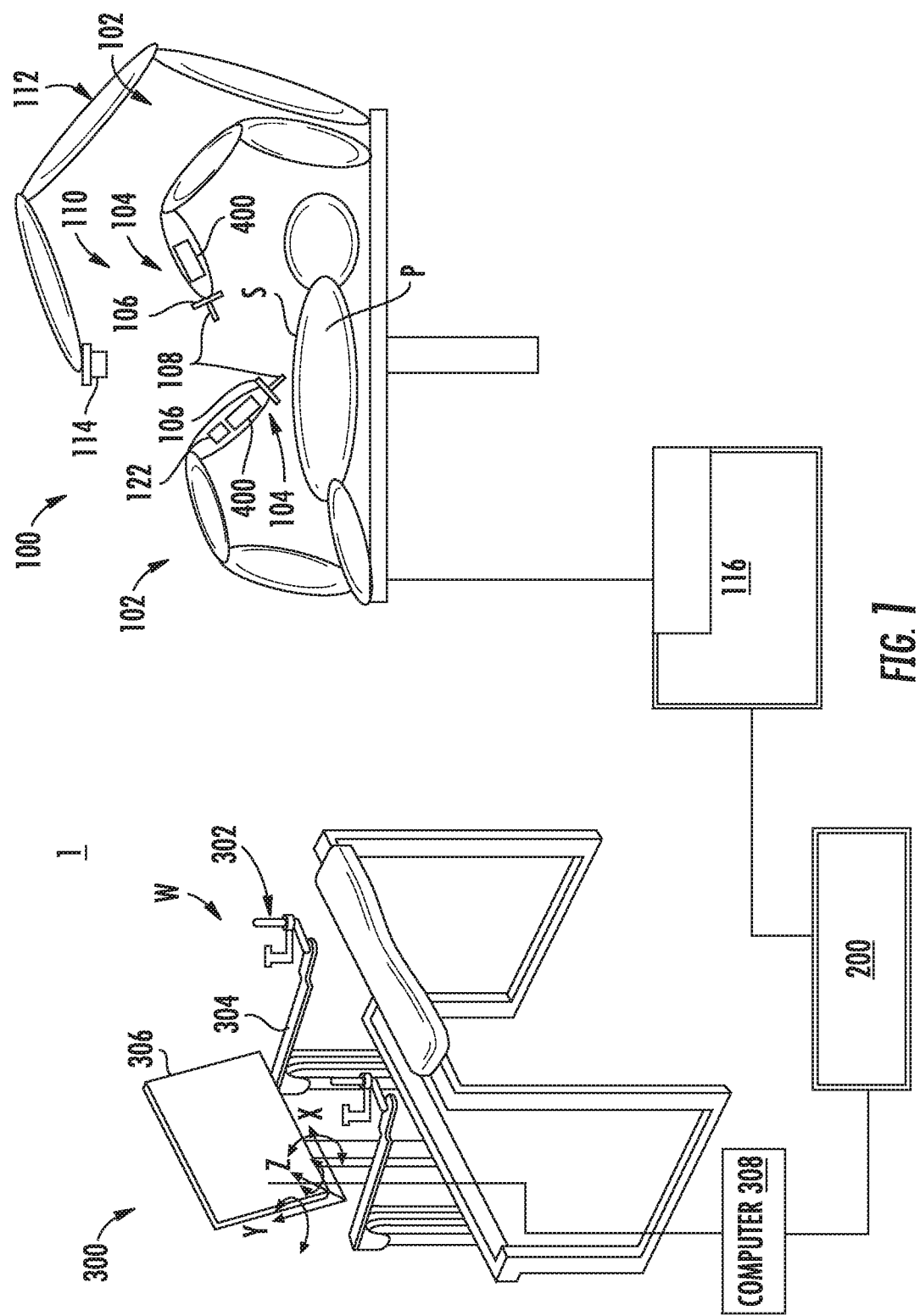
FIG. 1 is a schematic view of a robotic surgical system having a user console and a surgical robot provided in accordance with an embodiment of the present disclosure.

Embodiments of the present robotic surgical control systems are described in detail with reference to the drawings, in which like reference numerals designate identical or corresponding elements in each of the several views.

As used herein, the term "clinician" refers to a doctor, nurse, healthcare provider, support personnel, or other operators of the robotic surgical system described herein.

As used herein, the term "surgical field" refers to the space in which the surgical robot operates. Such space may include, but is not limited to, an operating room, surgical robot storage and/or maintenance facility, or other such spaces.

As used herein, the term "pose" refers to a position and orientation of a component within space or a workspace.

The present disclosure relates generally to the positioning of position sensors or encoders in a control arm of a robotic surgical system, and use thereof. The encoders are positioned between a transmission component associated with a drive motor of the control arm and an input handle supported by the control arm. The encoders communicate positional or encoder signals to a controller, which are indicative of the pose of a joint of the control arm. In response to the encoder signals, the controller determines a direction and velocity in which a clinician is moving the input handle. In response to the direction and velocity of movement of the input handle, the controller sends control signals to move a motor associated with the joint of the control arm, the motor applying a force to overcome the forces associated with the transmission components. The application of force by the motor may reduce or eliminate the resistance the clinician would otherwise encounter while moving the input handle.

Referring initially to FIG. 1, a robotic surgical system in accordance with the present disclosure is shown generally as robotic surgical system 1 and includes a surgical robot 100, a controller 200, and a user interface or console 300.

The surgical robot 100 generally includes a robotic cart or tower 116 which has linkages 112. The linkages 112 moveably support an end effector or tool 108 that is configured to act on tissue. The linkages 112 may form robotic arms 102 which are configured to act on tissue. Each robotic arm 102 may have an end 104 that supports the tool 108. In addition, the ends 104 of the robotic arms 102 may include an imaging device 106 to image a surgical site "S". Further, the ends 104 of the robotic arms 102 may include one or more motors 122 that apply force about joints "J" (FIG. 2) of the robotic arm to move and/or actuate the tools 108.

The console 300 communicates with the tower 116 via the controller 200. The console 300 includes a display 306 that is configured to display three-dimensional images which may include data captured by imaging devices 106, 114 positioned about the surgical field, e.g., an imaging device positioned within the surgical site "S", an imaging device positioned adjacent to the patient "P", and/or an imaging device 114 supported by an end 104 of a robotic arm 102. The imaging devices, e.g., imaging devices 106, 114, may capture visual images, infra-red images, ultrasound images, X-ray images, thermal images, and/or any other known real-time images of the surgical site "S". The imaging devices 106, 114 transmit captured imaging data to the controller 200 which generates three-dimensional images of the surgical site "S" in real-time from the imaging data and transmits the three-dimensional images to the display 306 for display.

The console 300 includes control arms 304 which moveably support input handles 302 in a workspace "W". The control arms 304 allow a clinician to manipulate the surgical robot 100, e.g., move the robotic arms 102, the ends 104 of the robotic arms 102, and/or the tools 108. Each of the input handles 302 is in communication with the controller 200 to transmit input signals thereto and receive output or feedback signals therefrom. Additionally or alternatively, each of the input handles 302 may allow the surgeon to manipulate, e.g., clamp, grasp, fire, open, close, rotate, thrust, slice, etc., the tools 108 supported at the ends 104 of the robotic arms 102.

With continued reference to FIG. 1, motion of each of the input handles 302 through the workspace "W" moves the ends 104 of the robotic arms 102 and/or tools 108 within a surgical site "S". The three-dimensional images on the display 306 are oriented such that movement of the input handles 302 moves the ends 104 of the robotic arms 102 as viewed on the display 306. The three-dimensional images may remain stationary while movement of the input handles 302 is scaled to movement of the ends 104 of the robotic arms 102 within the three-dimensional images. To maintain an orientation of the three-dimensional images, kinematic mapping of the input handles 302 is based on a camera orientation relative to an orientation of the ends 104 of the robotic arm 102. The orientation of the three-dimensional images on the display 306 may be mirrored or rotated relative to a view from above the patient "P". In addition, the size of the three-dimensional images on the display 306 may be scaled to be larger or smaller than the actual structures of the surgical site "S" permitting the clinician to have a better view of structures therein. As the input handles 302 are moved, the tools 108 are moved within the surgical site "S" as detailed below. Movement of the tools 108 may also include movement of the ends 104 of the robotic arms 102 which support the tools 108.

For a detailed discussion of the construction and operation of a robotic surgical system 1, reference may be made to U.S. Pat. No. 8,828,023, the entire disclosure of which is hereby incorporated by reference.

The movement of the input handles 302 may be scaled relative to the movement of the tools 108. When the input handles 302 are moved within the workspace "W", the control arm 304 transmits encoder signals to the controller 200, which analyzes the encoder signals and generates control signals to move the tools 108 in response to the encoder signals. The controller 200 transmits control signals to the tower 116 to move the tools 108 in response to the movement of the input handles 302. Prior to transmission of the control signals, the controller 200 scales the encoder signals by dividing an Input$_{distance}$, e.g., the distance moved by one of the input handles 302 within the workspace "W", by a scaling factor S$_F$ to arrive at a scaled Output$_{distance}$, e.g., the distance that one of the ends 104 is moved. The scaling factor S$_F$ may be in a range between about 1 and about 10, in embodiments, about 3. This scaling is represented by the following equation:

$$\text{Output}_{distance} = \text{Input}_{distance}/S_F$$

After the encoder signal is scaled, the controller 200 transmits control signals corresponding to the scaled encoder signal to the tower 116 to move the tools 108 accordingly. It will be appreciated that the larger the scaling factor S$_F$ the smaller the movement of the tools 108 relative to the movement of the input handles 302.

For a detailed description of scaling movement of the input handles 302 along the X, Y, and Z coordinate axis to movement of the tool 108, reference may be made to commonly owned International Patent Application Serial No. PCT/US2015/051130, filed on Sep. 21, 2015 (now International Patent Publication No. WO 2016/053657), and International Patent Application No. PCT/US2016/14031, filed Jan. 20, 2016, the entire disclosures of which are hereby incorporated by reference.

Figure 2:
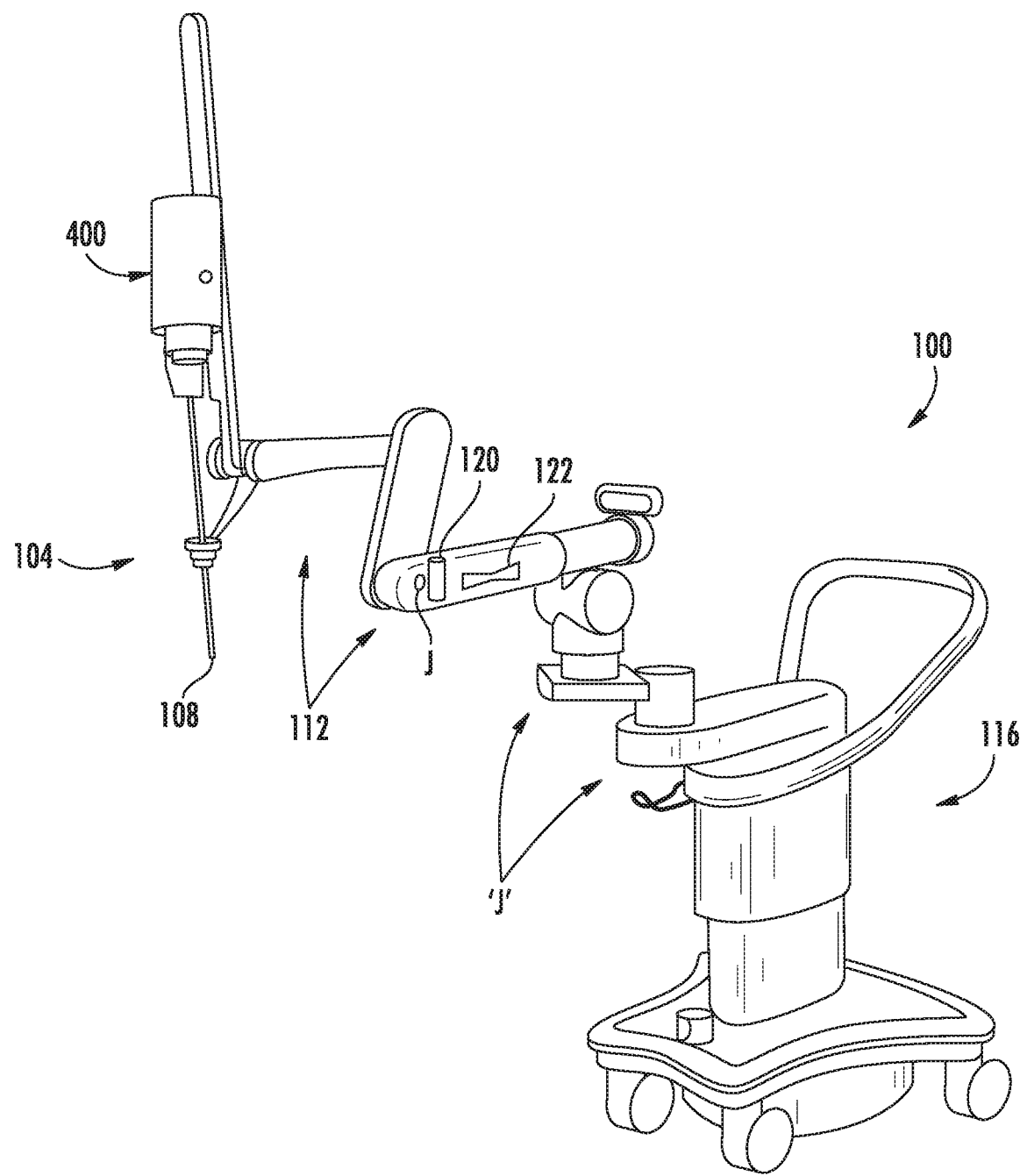
FIG. 2 is a perspective view of a tower of the surgical robot of FIG. 1.

Referring to FIG. 2, the surgical robot 100 includes the robotic cart or tower 116 supporting the linkages 112 which support the tool 108. The linkages 112 include one or more motors 122 that are each associated with a respective joint "J" of the linkage 112, to manipulate the linkage 112 and/or the tool 108 supported by the linkage 112.

In use, the controller 200 (FIG. 1) transmits control signals to the surgical robot 100. The surgical robot 100 activates a motor 122 to apply a force about or to a respective joint "J" in response to the control signals. Specifically, in response to a control signal, the surgical robot 100 delivers a power current to the motor 122 which applies a force to the joint "J" to move the linkage 112 and/or the tool 108 during a surgical procedure. Additionally, a sensor 120 is coupled to the joint "J" and measures a force about the joint "J" in response to application of the force to the joint "J". The sensor 120 transmits the measured force to the controller 200 (FIG. 1).

Figure 3:
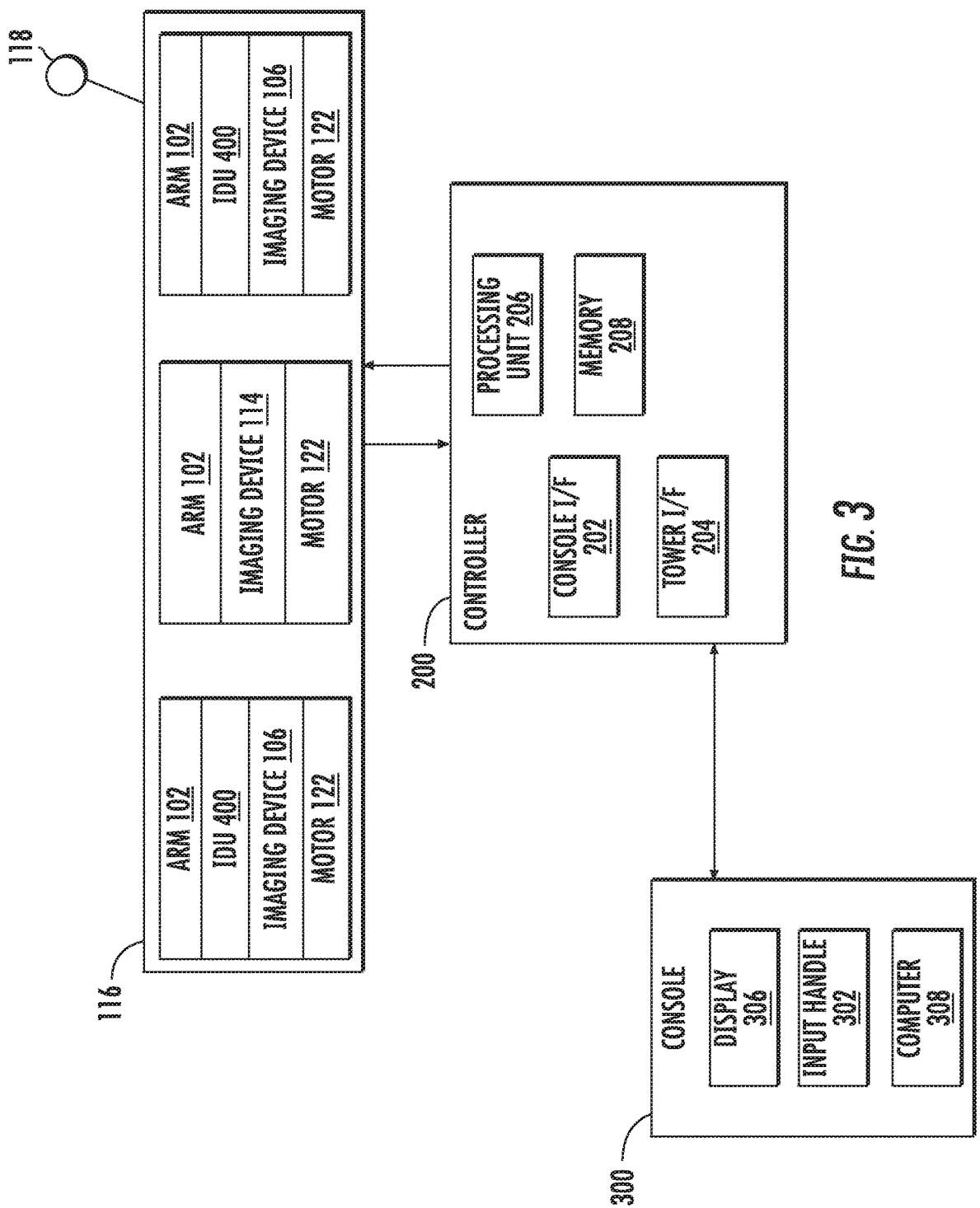
FIG. 3 is a functional block diagram of a system architecture for controlling the robotic surgical system of FIG. 1.

With reference to FIG. 3, communication between the surgical robot 100, the console 300, and the controller 200 is described in accordance with the present disclosure. The controller 200 is in communication with the tower 116 of the surgical robot 100 to provide instructions for operation of the surgical robot 100 in response to encoder signals received from the console 300.

The controller 200 generally includes a processing unit 206, a memory 208, a tower interface 204, and a console interface 202. The processing unit 206 executes instructions or a computer program stored in the memory 208 which functions to cause components of the tower 116, e.g., linkages 112, to execute desired movements according to movement defined by the input handle 302 of the console 300. In this regard, the processing unit 206 includes any suitable logic control circuit adapted to perform calculations and/or operate according to a set of instructions. The processing unit 206 may include one or more processing devices (not shown) such as a microprocessor or other physical device capable of executing instructions stored in the memory 208 and/or processing data. The memory 208 may include transitory type memory, e.g., RAM, and/or non-transitory type memory, e.g., flash media or disk media. The tower interface 204 and console interface 202 communicate with the tower 116 and console 300, respectively, via either wireless configurations, e.g., radio frequency, optical, WIFI, Bluetooth® (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)), etc., and/or wired configurations. Although depicted as a separate module, the console interface 202 and tower interface 204 may be a single component.

With continued reference to FIGS. 2-3, the tower 116 includes a communications interface 118 that receives communications and/or data from the tower interface 204. The communications interface 118 transmits signals which manipulate the motor 122 to move the linkages 112 associated with the tower 116. The motor 122 may be located in the robotic arm 102 and/or the linkages 112. In embodiments, the motor 122 mechanically manipulates the robotic arm 102, the linkages 112, and/or the tool 108 (FIG. 1) in response to power supplied to the motor 122. Mechanical manipulation of the robotic arm 102, linkages 112, and/or the tool 108 may include application of force from the motor 122 to move the robotic arm 102 and/or the tool 108 coupled to the robotic arm 102, in response to instructions from the processing unit 206. For example, the motor 122 may be operably coupled to a joint "J" via cables (not shown) to manipulate the robotic arm 102.

Figure 4:
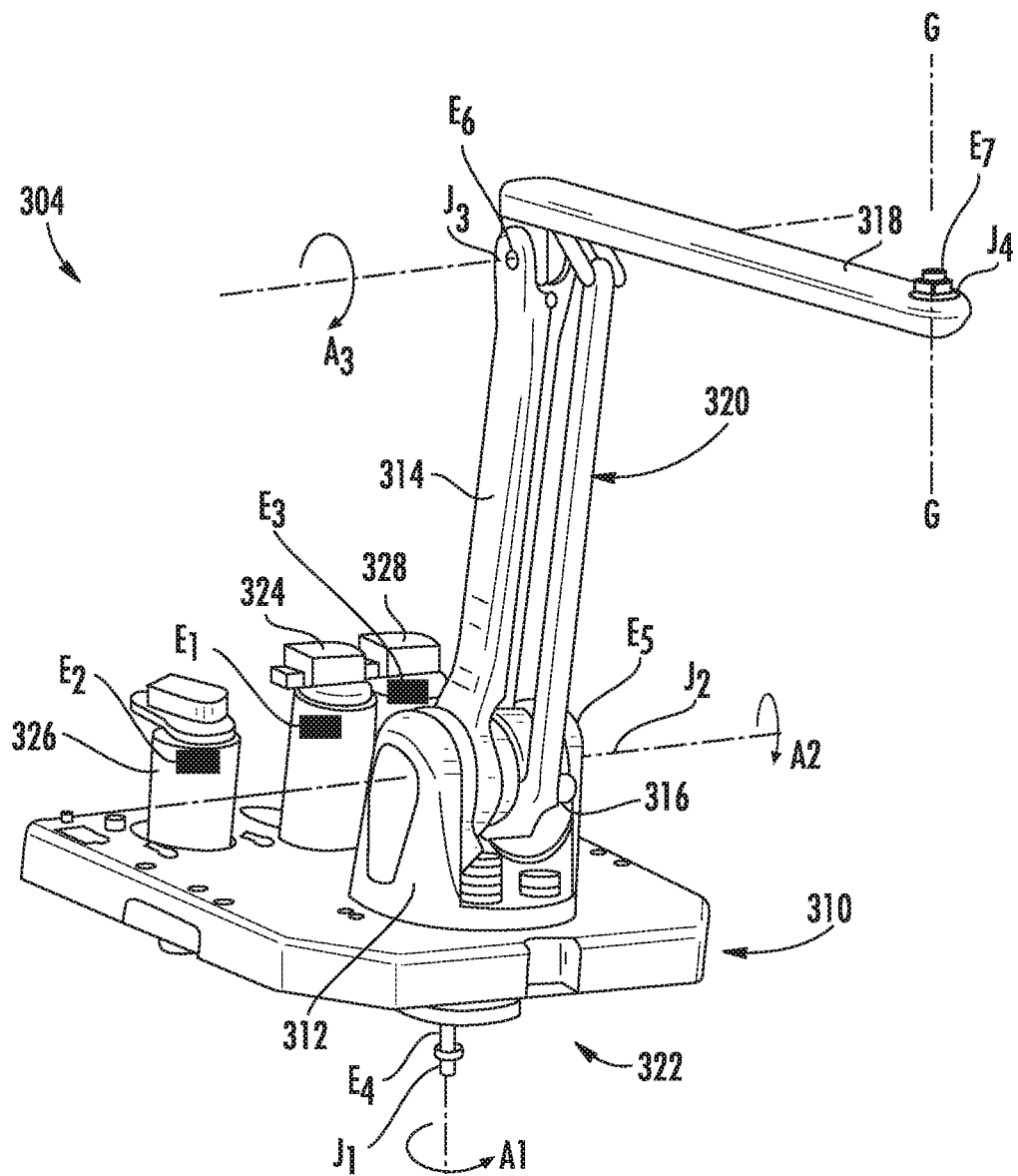
FIG. 4 is a perspective view of a control arm of the user console of FIG. 1 with covers removed.
Figure 5:
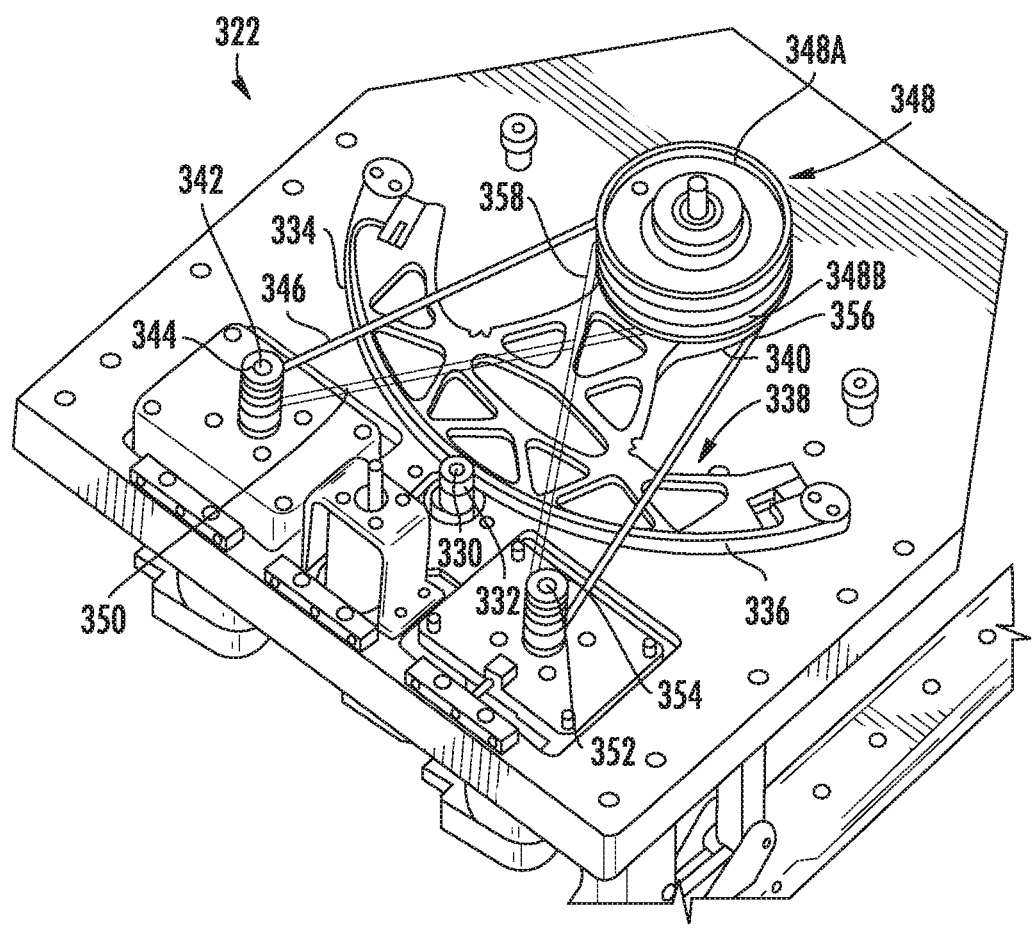
FIG. 5 is a lower perspective view of a control arm base of the control arm of FIG. 4.

The console 300 includes a computer 308 to receive encoder signals from position sensors or encoders $E_1$, $E_2$, $E_3$, transmit the encoder signals to the controller 200, and receive control signals from the controller 200 to move members, e.g. the of the control arm 304, about joints $J_1$, $J_2$, $J_3$ (FIG. 4-5). Each input handle 302 is coupled to the control arm 304. The control arm 304 includes a first, second, and third drives motors 324, 326, 328 that are in either wired or wireless communication with the computer 308. The encoders $E_1$, $E_2$, $E_3$ are disposed in the drive motors 324, 326, 328, respectively, and are configured to generate encoder signals representative of the pose of the members of the control arm 304 (FIG. 4-5) associated with joints $J_1$, $J_2$, $J_3$. The encoder signals representing the pose of the members of the control arm 304 about joints $J_1$, $J_2$, $J_3$ are transmitted by the encoders $E_1$, $E_2$, $E_3$ to the computer 308 which transmits the encoder signals to the controller 200. In response to the encoder signals, the controller 200 transmits control signals to the tower 116 to affect motion of the robotic arm 102 and/or the tools 108 as detailed above.

The input handle 302 may be a handle, a pedal, or a computer accessory (e.g., a keyboard, joystick, mouse, button, touch screen, switch, trackball, etc.). The display 306 displays images or other data received from the controller 200 to communicate data to the clinician. The computer 308 includes a processing unit and memory (not shown) which includes data, instructions, and/or information related to the various components, algorithms, and/or operations of the tower 116 and can operate using any suitable electronic service, database, platform, cloud, or the like. The computer 308 may include processing units (not shown) which include any suitable logic control circuit adapted to perform calculations and/or operate according to a set of instructions located in memory (not shown) as described similarly with reference to the controller 200.

For a detailed description of a surgical robot 100, reference may be made to U.S. Provisional Patent Application No. 62/345,032, filed Jun. 3, 2016, and entitled "Multi-Input Robotic Surgical System Control Scheme," the entire disclosure of which is hereby incorporated by reference.

Referring to FIG. 4-5, a control arm 304 of the console 300 includes a base 310, a swivel member 312, a vertical member 314, a support arm 316, a horizontal member 318, and a support member 320 (collectively referred to as "members of control arm 304"). The base 310 rotatably supports the swivel member 312 about a first joint $J_1$ defining a first axis of rotation $A_1$. The swivel member 312 pivotally supports the vertical member 314 and the support arm 316 about a second joint $J_2$ defining a second axis of rotation $A_2$. The support arm 316 supports a lower end of the support member 320 which may be in substantial parallel relationship with the vertical member 314. It is contemplated that the support member 320 may be askew from the vertical member 314. The vertical member 314 pivotally supports the horizontal member 318 about a third joint $J_3$ defining a third axis of rotation $A_3$. The horizontal member 318 rotatably supports the input handle 302 (FIG. 1) about a joint $J_4$ defining a fourth axis of rotation G-G.

The base 310 includes a drive mechanism 322 for manipulating the control arm 304 about each of the first, second, and third axes of rotation $A_1$, $A_2$, $A_3$. The drive mechanism 322 may manipulate the control arm 304 to provide force feedback to the clinician manipulating the control arm 304 via the input handle 302 (FIG. 1). The drive mechanism 322 may also manipulate the control arm 304 to reposition components of the control arm 304 during a surgical procedure.

The drive mechanism 322 includes a first drive motor 324, a second drive motor 326, and a third drive motor 328. The first drive motor 324 manipulates the control arm 304 about the first axis of rotation $A_1$ and includes a first drive shaft 330 that extends through the base 310. The first drive shaft 330 rotates a first spindle 332 that is coupled to a first cable 334 and a second cable 336 that rotate a rotation flange 338 about the first axis of rotation $A_1$. The rotation flange 338 includes a cylindrical member 340 that couples to the swivel member 312 such that the swivel member 312 rotates in concert with the cylindrical member 340.

The second drive motor 326 manipulates the vertical member 314 of the control arm 304 about the second axis $A_2$ and includes a second drive shaft 342 that extends through the base 310. The second drive shaft 342 rotates a second spindle 344 that is coupled to a third cable 346 and a fourth cable 350 to rotate a lower pulley 348A of the pulley assembly 348. The lower pulley 348A is operably coupled to the vertical member 314 to pivot the vertical member 314 about the second axis of rotation $A_2$ in response to rotation of the lower pulley 348A.

The third drive motor 328 manipulates the support arm 316 to pivot the horizontal member 318 about the third axis $A_3$ and includes a third drive shaft 352 that extends through the base 310. The third drive shaft 352 rotates a third spindle 354 that is coupled to a fifth cable 356 and a sixth cable 358 to rotate an upper pulley 348B of the pulley assembly 348. The upper pulley 348B is operably coupled to the horizontal member 318 to pivot the horizontal member 318 about the third axis $A_3$ in response to rotation of the upper pulley 348B.

For a detailed description of control arm 304, reference may be made to U.S. Provisional Patent Application No. 62/345,537, filed Jun. 3, 2016, and entitled "Control Arm for Robotic Surgical Systems," the entire disclosure of which is hereby incorporated by reference.

With continuing reference to FIG. 5, the base 310 includes motor encoders $E_1$, $E_2$, $E_3$ that are each associated with a respective drive motor 324, 326, 328. The first, second, and/or third encoder $E_1$, $E_2$, $E_3$ may be disposed within or external to the first drive motor 324, the second drive motor 326, or third drive motor 328, respectively. The first motor encoder $E_1$ transmits encoder signals to the computer 308 which measures the pose and/or velocity of the first drive shaft 330. The second motor encoder $E_2$ transmits encoder signals to the computer 308 which measures the pose and/or velocity of the second drive shaft 342. The third motor encoder $E_3$ transmits encoder signals to the computer 308 which measures the pose and/or velocity of the third drive shaft 352. Additionally or alternatively the first, second, and third motor encoders $E_1$, $E_2$, $E_3$ may be in direct communication with the controller 200 to transmit encoder signals measured by the respective encoders $E_1$, $E_2$, $E_3$ to the controller 200 (FIG. 1). In response to receiving the positional signals, the controller 200 may determine the corresponding pose, velocity, or direction of rotation of the respective drive shaft 330, 342, 352.

To accurately determine the pose of components or members of the control arm 304, e.g., the swivel member 312, the vertical member 314, and/or the horizontal member 318, the control arm 304 includes joint encoders $E_4$, $E_5$, $E_6$ (collectively referred to as joint encoders) are each coupled to a respective one of the first, second, and third joints $J_1$, $J_2$, $J_3$ of the control arm 304. Specifically, the first joint encoder $E_4$ is configured to determine the pose and/or the velocity of the base 310 and the swivel member 312 about the first joint $J_1$, the second joint encoder $E_5$ is configured to determine the pose and/or the velocity of the vertical member 314 and the support arm 316 about the second joint $J_2$, and the third joint encoder $E_6$ is configured to determine the pose and/or the velocity of the vertical member 314 and the horizontal member 318 rotating about the third joint $J_3$. As the clinician manipulates the input handle 302, the swivel member 312, vertical member 314, and/or horizontal member 318 may rotate about the first, second, and third joints $J_1$, $J_2$, $J_3$, respectively.

For purposes of brevity, only motion of the swivel member 312 and the base 310 about the first axis $A_1$ will be described in detail herein. Specifically, with reference to FIGS. 4 and 5, the rotation of the swivel member 312 about the first axis $A_1$ is described in accordance with the present disclosure. As the swivel member 312 rotates about the first joint $J_1$, the first joint encoder $E_4$ transmits encoder signals to the controller 200. In response to the encoder signals, the controller 200 determines the pose, direction, and/or velocity of the swivel member 312.

As the clinician manipulates the input handle 302, the swivel member 312 can be rotated about the first axis $A_1$ such that corresponding transmission components associated with the swivel member, e.g., the cylindrical member 340, the rotation flange 338, the second cable 336, the first cable 334, the first spindle 332, and the first drive shaft 330, may rotate in response to rotation of the swivel member 312 to backdrive the first drive motor 324. As the transmission components are rotated, compliance in the transmission, e.g., elastic deformation of the transmission components such as binding, lashing, and/or compression, may delay backdriving of the first drive motor 324 in response to input from the input handle 302. The delay in the backdriving of the first drive motor 324 may result in a positional error between the first drive motor 324 and the joint $J_1$. The positional error may be measured by calculating the difference between encoder signals sent from the first motor encoder $E_1$ and the joint encoder $E_4$.

Figure 6:
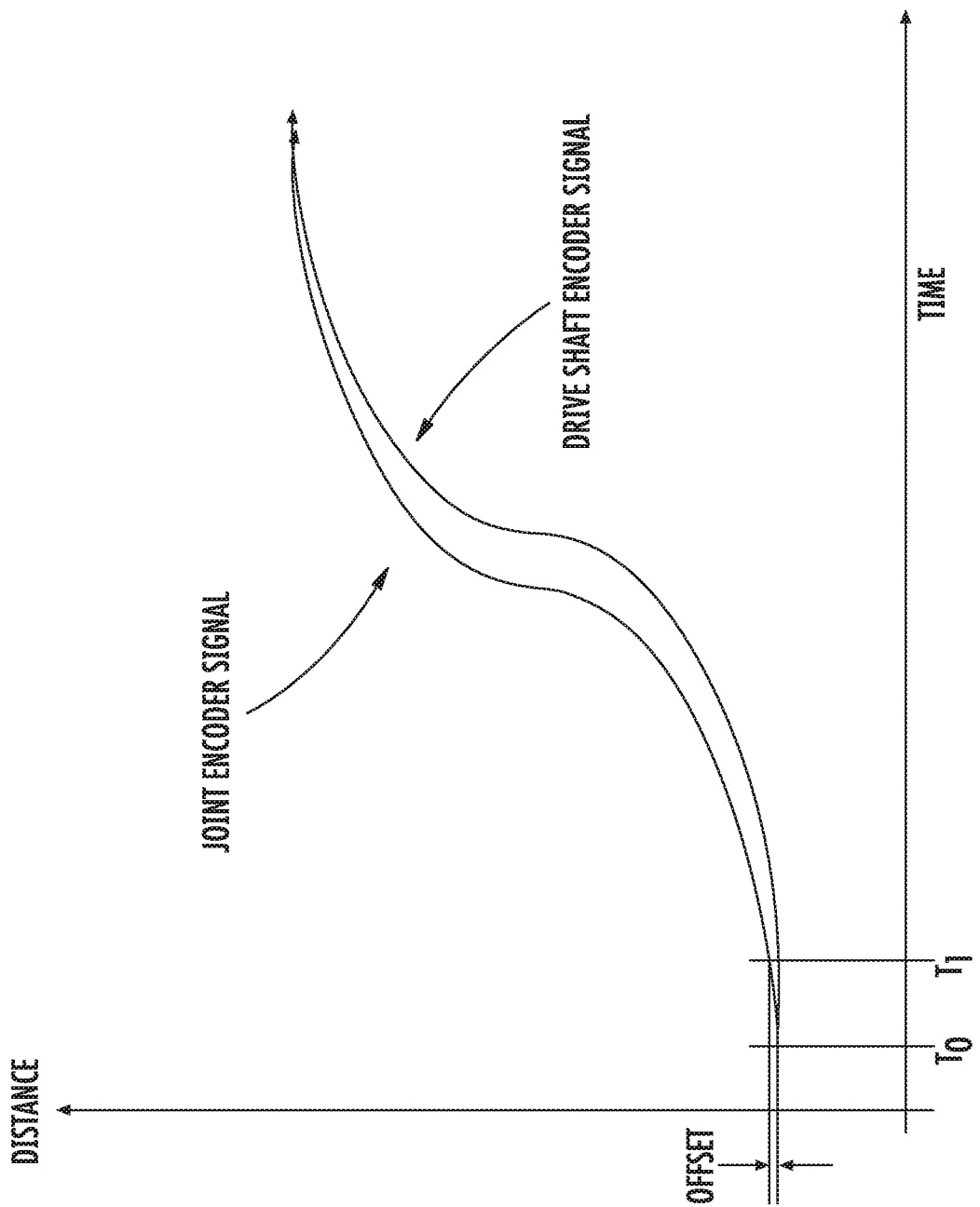
FIG. 6 is a position diagram of the position of the control arm of FIG. 4 and the position of one of the motors of the control arm of FIG. 5 over time.

Referring to FIG. 6, as the clinician manipulates the pose of the input handle 302 supported by the control arm 304, the swivel member 312 is rotated relative to the base 310 about the first axis $A_1$. The pose of the swivel member 312 and the base 310 about the first joint $J_1$ is measured by the first joint encoder $E_4$ which transmits encoder signals to the computer 308. As shown, rotation of the first drive motor 324 in response to movement of the input handle 302 is delayed due to compliance in the transmission components. The delay occurs between time $T_0$ and time $T_1$, resulting in an offset distance defined as the distance which the swivel member 312 moves about the first joint $J_1$ before the first drive motor 324 moves in response to the movement of the swivel member 312.

The offset distance may be a predetermined distance which is measurable during initial or periodic calibration of the control arm 304. For example, the display 306 may prompt the clinician to move the control arm 304 to one or more poses, the controller 200 measuring position data from the first joint encoder $E_4$ and the first motor encoder $E_1$. In response to receiving the encoder signals from the first joint encoder $E_4$ and the first motor encoder $E_1$, the controller 200 calculates an offset distance associated with motion of input handle 302 about the first axis $A_1$ to a desired pose. Additionally or alternatively, the controller 200 may send control signals to the first drive motor 324 to move the input handle 302 about the first axis $A_1$ to a pose. In response to moving the input handle 302 to a desired pose, the controller 200 calculates the offset distance associated with the motion of the swivel member 312 and the base 310 about the first joint $J_1$ relative to the first drive motor 324.

Specifically, in response to manipulation of the input handle 302 by the clinician, the controller 200 may more accurately determine the position of the first drive motor 324 relative to the swivel member 312 and the base 310, and transmit control signals as the clinician moves the input handle 302 about the workspace "W" to adjust the position of the first drive motor 324. This adjustment of the position of the motor relative to the swivel member 312 and the base 310 corrects for any compliance in the transmission components.

Figure 7:
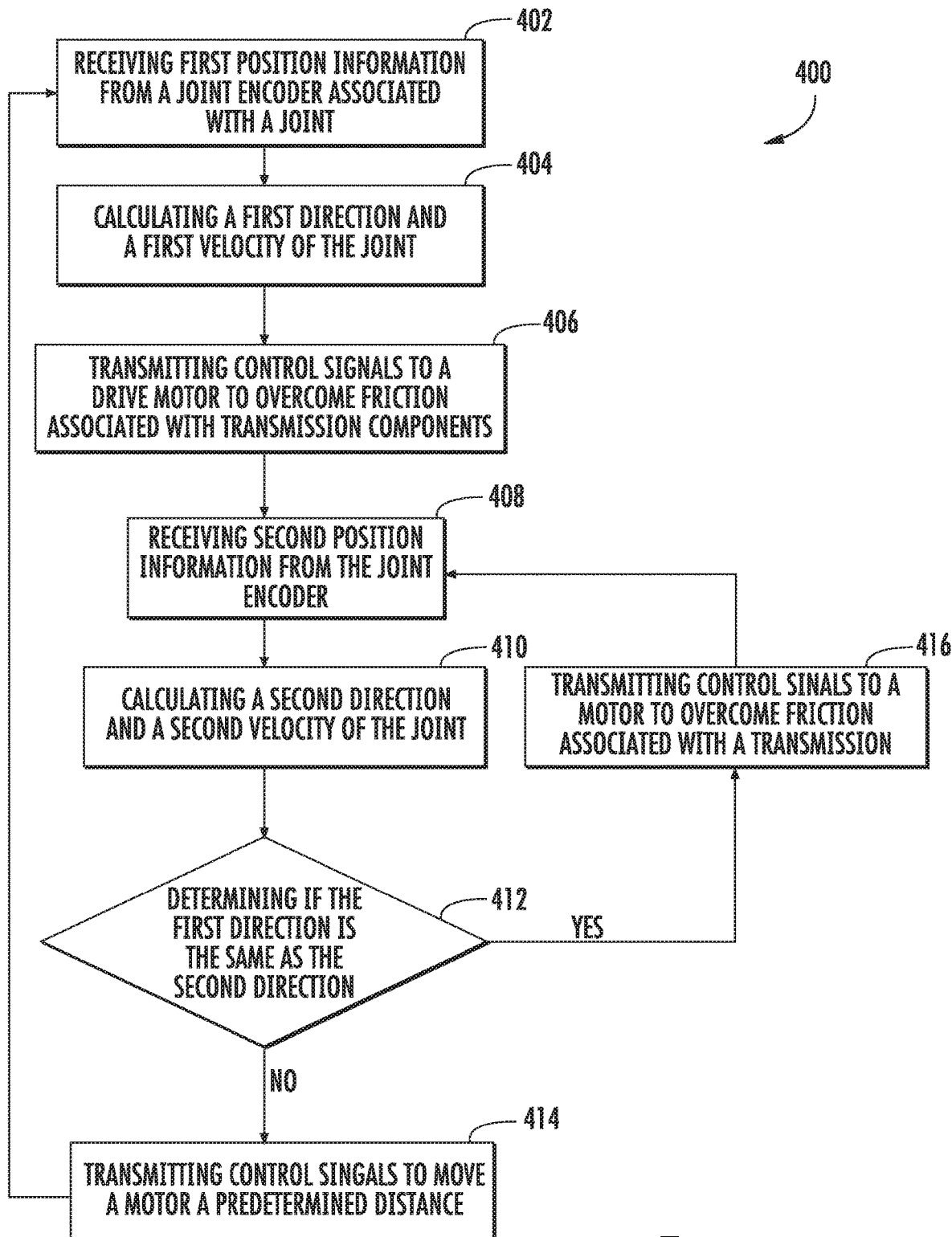
FIG. 7 is a flow chart illustrating a method of compensating for friction in a transmission component.

Referring to FIG. 7, a method 400 of compensating for friction in a transmission component is described in accordance with the present disclosure. The transmission friction is defined as the friction associated with rotation of the transmission components. Initially, the controller 200 receives first position information from the joint encoder $E_4$ (Step 402) and calculates a first direction and a first velocity of the swivel member 312 about the base 310 at the first joint $J_1$ (Step 404). After calculating the first direction and the first velocity of the swivel member 312 relative to the base 310 at the joint $J_1$, the controller 200 transmits control signals to rotate the first drive motor 324 to compensate for friction of a transmission component. Specifically, in response to the control signals, the first drive motor 324 applies a force in the direction which the swivel member 312 is moving relative to the base 310 at the first joint $J_1$ to overcome an estimated friction or transmission friction of the transmission components (Step 406).

Specifically, method 400 helps minimize a friction felt by a surgeon when changing a direction of movement of the input handle 302 and the control arm 304. If the first motor encoder $E_1$ were used only, then the surgeon would feel the full level of friction in the input handle 302 and in the control arm 304 when changing a direction of movement of the input handle 302 and/or the control arm 304, whereby the joint and the drive train must all be moving in order for a friction thereof to go from positive-to-negative to negative-to-positive. However, in accordance with the present disclosure, and in accordance with method 400, the time and friction observed and/or measured is reduced by measuring and monitoring a change in direction of the joint encoder $E_4$, as compared to that of the first motor encoder $E_1$.

After the controller 200 transmits control signals to overcome the estimated friction, the controller 200 receives second position information from the joint encoder $E_4$ (Step 408). In response to receiving the second position information, the controller 200 calculates a second direction and a second velocity of the swivel member 312 relative to the base 310 at the first joint $J_1$ (Step 410). When the controller 200 determines the second direction is the same as the first direction (Step 412), the controller 200 transmits control signals to the first drive motor 324 to overcome an estimated friction associated with rotation of the transmission components operably coupling the first drive motor 324 to the input handles 302 at the second velocity (Step 416). It will be appreciated that when the first velocity and/or the second velocity are equal to zero, the control signals transmitted by the controller 200 to overcome the estimated friction will not cause the first drive motor 324 to rotate.

With continued reference to FIG. 7, when the controller 200 determines that the first direction and the second direction are different (Step 412), the controller 200 transmits control signals to rotate the first drive motor 324 a predetermined distance in the second direction (Step 414). The predetermined distance may be a distance equal to the offset distance measured during initial or periodic calibration of the control arm 304 (FIG. 6). Rotation of the first drive motor 324 in the second direction reduces or eliminates positional errors between the first drive motor 324, the swivel member 312 and the base 310 which may otherwise exist as a result of compliance in the transmission components. By reducing or eliminating positional errors due to compliance, the control signals sent by the controller 200 allow for more accurate application of force by the first drive motor 324 to overcome transmission friction. As a result, the clinician may feel as if the input handle 302 is more responsive than would otherwise be due to transmission friction.

Figure 8:
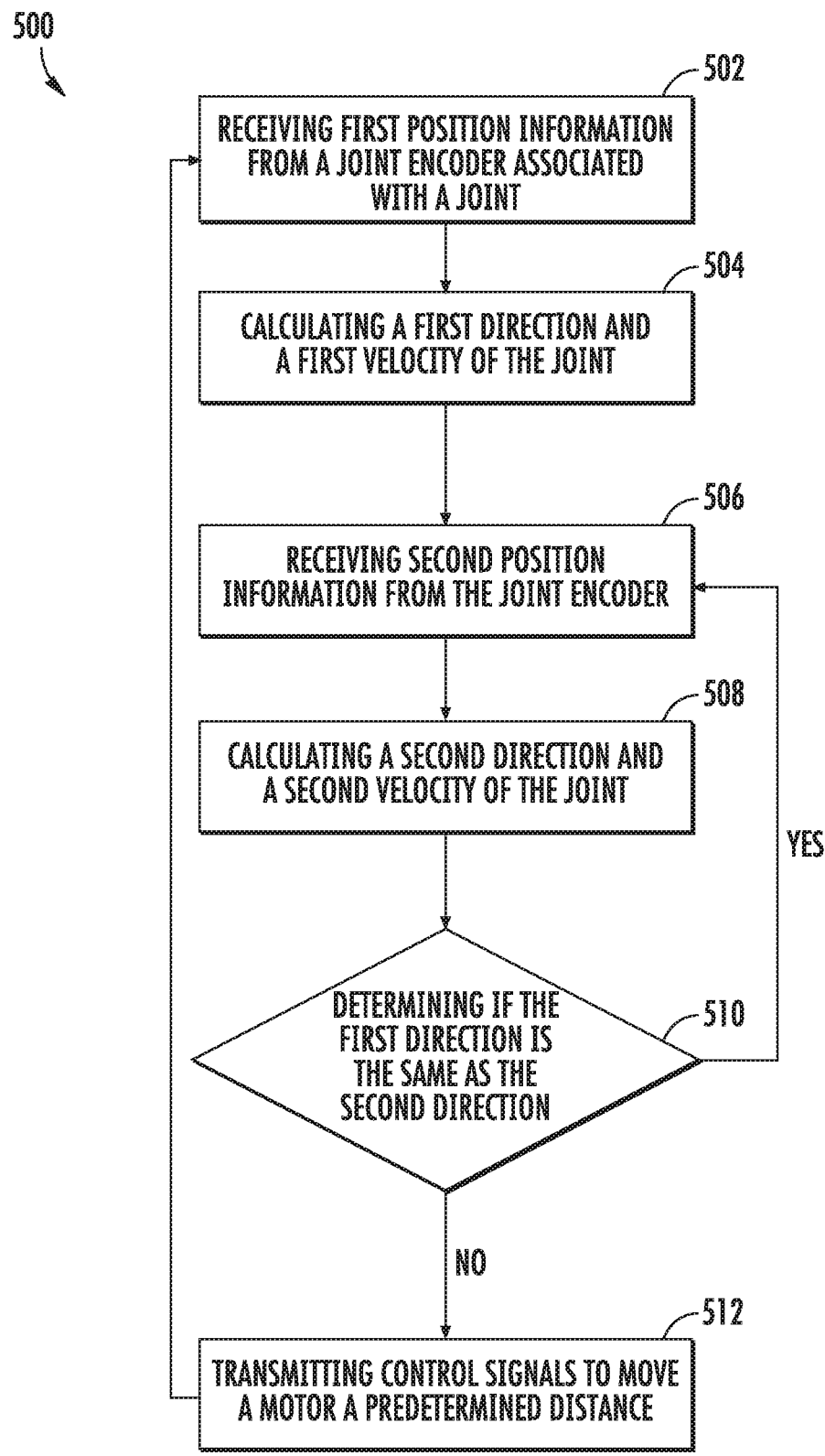
FIG. 8 is a flow chart illustrating a method of compensating for positional offsets.

Referring to FIG. 8, a method of compensating for positional offsets is described in accordance with the present disclosure. Initially, the controller 200 receives first position information from the joint encoder $E_4$ (Step 502). In response the controller 200 calculates a first direction of the swivel member 312 relative to the base 310 about the first joint $J_1$. The controller 200 subsequently receives second position information from the joint encoder $E_4$ (Step 506) and calculates a second direction of the members of the control arm 304 associated with the first joint $J_1$. If the controller 200 determines that the first direction and the second direction are different (Step 510), the controller 200 transmits control signals to rotate the first drive motor 324 a predetermined distance in the first direction (Step 512). The predetermined distance may be a distance equal to the offset distance (FIG. 6). By rotating the first drive motor 324 the predetermined distance in the first direction, as the clinician subsequently manipulates the input handles 302 and backdrives the first drive motor 324, the application of force feedback by the first drive motor 324 is applied almost instantaneously, thereby allowing for more accurate application of force feedback. Specifically, the application of force feedback to the input handle 302 is not delayed due to any compliance in the transmission components.

While method 400 of compensating for friction in a transmission component and method 500 of compensating for positional offsets have been described in relation to motion of the swivel member 312 about the base 310 along the first axis of rotation $A_1$, the present disclosure should not be seen as limited to the identified components. It will be appreciated that methods 400, 500 may also be applied to motion of the vertical member 314 and the support arm 316 relative to the swivel member 312 about the second axis of rotation $A_2$. Additionally, it will be appreciated that methods 400, 500 may be applied to motion of the horizontal member 318 relative to the vertical member 314 about the third axis of rotation $A_3$.

While the disclosed embodiments contemplate location of a controller 200 external to a surgical robot 100, it is contemplated that the controller 200 may be located within the control arm 304, or alternatively that elements of the robotic surgical system 1 may include circuitry which executes the described encoder measurements and calculations independent of the controller 200.

As detailed above, the console 300 is in operable communication with the surgical robot 100 to perform a surgical procedure on a patient; however, it is envisioned that the console 300 may be in operable communication with a surgical simulator (not shown) to virtually actuate a surgical robot and/or tool in a simulated environment. For example, the robotic surgical system 1 may have a first mode in which the console 300 is coupled to actuate the surgical robot 100 and a second mode in which the display 306 is coupled to the surgical simulator to virtually actuate a robotic surgical system. The surgical simulator may be a standalone unit or be integrated into the controller 200. The surgical simulator virtually responds to a clinician interfacing with the console 300 by providing visual, audible, force, and/or haptic feedback to a clinician through the console 300. For example, as a clinician interfaces with the input handles 302, the surgical simulator moves representative tools that are virtually acting on tissue. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

Additionally, while the application refers to members of the control arm as receiving and propagating forces received by the input handle through transmission components generally, the identified members of the control arm have been identified for illustrative purposes only and are not intended to limit the disclosure. As such, members of the control arm should be understood generally to be components of the control arm 304 which may receive forces exerted by a clinician thereon. Likewise, the identified transmission components are identified for illustrative purposes only and are not intended to limit the disclosure. As such, transmission components should be understood generally to be components which propagate forces received by members of the input components to the first, second, and/or third drive motors 324, 326, 328.

It is contemplated that the systems and methods described in the present disclosure may be implemented in robotic surgical systems which implement telemanipulation techniques. "Telemanipulation" refers generally to the operation of a surgical system from a remote console by a clinician. By way of example, a telemanipulation may be a remote adjustment of the position of a robotic surgical instrument relative to a patient. Alternatively, telemanipulation may include an individual causing a robotic surgical instrument to perform one or more functions which the instrument is capable of doing.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A control arm of a robotic surgical system, comprising:
   a member supported about a first joint and including an input handle extending therefrom, the input handle manipulatable by a user to move the member about the first joint to control movement of a robotic arm;
   a drive motor operably coupled to the member and configured to rotate the member about the first joint;
   a motor encoder configured to measure motor position and transmit motor position signals;
   a first joint encoder disposed about the first joint, the first joint encoder configured to measure joint position and transmit position signals indicative of a pose of the member about the first joint; and
   a controller configured to transmit control signals to the drive motor for rotating the member and the input handle about the first joint and for controlling movement of the robotic arm based on position signals from the first joint encoder and the motor position signals from the motor encoder.

2. The control arm of claim 1, further comprising a transmission component disposed between the drive motor and the first joint to couple the member to the drive motor.

3. The control arm of claim 2, wherein the controller is configured to transmit control signals to overcome a friction associated with the transmission component for moving the member about the first joint.

4. The control arm of claim 2, wherein the drive motor is coupled to the transmission component at a second joint.

5. The control arm of claim 4, wherein the motor encoder is coupled to the drive motor at the second joint.

6. The control arm of claim 1, wherein the controller is configured to calculate a direction of the member moving about the first joint.

7. The control arm of claim 6, wherein the controller is configured to generate control signals to overcome transmission friction in response to calculating the direction of the member moving about the first joint.

8. The control arm of claim 6, wherein the controller is configured to calculate a velocity of the member moving about the first joint.

9. The control arm of claim 8, wherein the controller is configured to generate control signals to overcome transmission friction in response to calculating the direction and the velocity of the member about the first joint.

10. A method of compensating for friction in a transmission component of a surgical robotic system, the method comprising:
    receiving, at a controller, first position information of a member moving about a first joint from a joint encoder disposed about the first joint, the member including an input handle manipulatable by a user to move the member about the first joint to control movement of a robotic arm, the member coupled to a drive motor at the first joint by a transmission component;
    receiving, at the controller, motor position information of the drive motor from a motor encoder;
    calculating, at the controller, a positional error based on a difference between the first position information and the motor position information;
    calculating, at the controller, a first direction and a first velocity of the member based on the positional error and the first position information;
    causing the drive motor to overcome transmission friction associated with the transmission component cooperating with movement of the member based on a control signal; and
    causing the member and the input handle to rotate about the first joint and to move the robotic arm based on the control signal.

11. The method according to claim 10, further comprising:
   receiving, at the controller, second position information from the joint encoder in response to the member moving about the first joint;
   calculating, at the controller, a second direction and a second velocity of the member moving about the first joint; and
   comparing, at the controller, the first direction to the second direction.

12. The method according to claim 11, further comprising transmitting control signals from the controller to move the drive motor a predetermined distance in the second direction when the first direction is different from the second direction.

13. A method of compensating for positional offsets between a member and a drive motor of a surgical robotic system, the method comprising:
   receiving, at a controller, first position information from a first joint encoder disposed about a first joint, the first joint operably coupling a member to a drive motor, the member including an input handle manipulatable by a user to move the member about the first joint to control movement of a robotic arm;
   receiving, at the controller, motor position information of the drive motor from a motor encoder;
   calculating, at the controller, a positional error based on a difference between the first position information and the motor position information;
   calculating, at the controller, a first direction of movement of the member about the first joint based on the positional error and the first position information;
   receiving, at the controller, second position information from the first joint encoder;
   calculating, at the controller, a second direction of movement of the member about the first joint;
   comparing, at the controller, the first direction of movement to the second direction of movement;
   causing the drive motor to move a predetermined distance in the first direction of movement when the first direction of movement is different from the second direction of movement based on a control signal; and
   causing the member and the input handle to rotate about the first joint and to move the robotic arm based on the control signal.

14. The method according to claim 13, wherein causing the drive motor to move includes rotating the drive motor the predetermined distance in the first direction of movement, the drive motor coupled to a transmission component at a second joint.

15. The method according to claim 13, wherein causing the drive motor to move includes rotating the drive motor the predetermined distance, where the predetermined distance is equal to an offset distance.

* * * * *